United States Patent [19]

Carson

[11] Patent Number: 4,663,334

[45] Date of Patent: May 5, 1987

[54] HETEROAROMATIC ACETYLENES USEFUL AS ANTIHYPERTENSIVE AGENTS

[75] Inventor: John R. Carson, Norristown, Pa.

[73] Assignee: McNeilab, Inc., Fort Washington, Pa.

[21] Appl. No.: 807,551

[22] Filed: Dec. 11, 1985

[51] Int. Cl.$^4$ .................... A61K 31/40; A61K 31/33; C07D 211/84; C07D 227/02; C07D 217/12; C07D 217/22; C07D 209/12; C07D 209/04

[52] U.S. Cl. .................... 514/357; 514/349; 514/350; 514/351; 514/354; 514/356; 514/423; 514/424; 514/426; 514/427; 546/300; 546/334; 546/312; 546/141; 548/375; 548/378; 548/543; 548/557; 548/558; 548/561; 548/483; 548/484; 544/406; 544/408; 544/409; 544/336; 546/143; 546/146; 546/149; 546/153; 546/156; 546/157; 546/158; 546/159; 546/162; 546/164; 548/493; 548/503; 548/506; 544/298; 544/315; 544/319; 544/334; 544/335

[58] Field of Search .................. 546/300, 334, 312; 548/375, 378, 543, 557, 558, 561; 514/349, 350, 351, 354, 356, 357, 423, 424, 426, 427, 428

[56] References Cited

U.S. PATENT DOCUMENTS

| | | | |
|---|---|---|---|
| 3,590,084 | 6/1971 | Peperkamp et al. | 260/570.7 |
| 3,914,432 | 10/1975 | Koppe et al. | 424/304 |
| 3,959,338 | 5/1976 | Koppe et al. | 260/465 |
| 4,010,158 | 3/1977 | Koppe et al. | 260/253 |
| 4,412,856 | 11/1983 | Brunner et al. | 71/121 |

FOREIGN PATENT DOCUMENTS

| | | |
|---|---|---|
| 2503222 | 7/1976 | Fed. Rep. of Germany . |
| 3006351 | 9/1981 | Fed. Rep. of Germany . |
| 813564 | 5/1981 | South Africa . |

*Primary Examiner*—Henry R. Jiles
*Assistant Examiner*—J. Richter
*Attorney, Agent, or Firm*—David J. Levy

[57] ABSTRACT

Heterocyclic acetylenes of the formula (I):

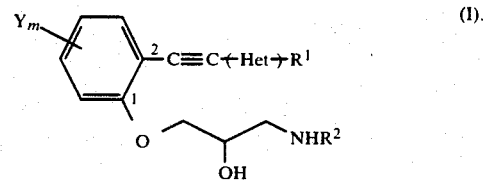

wherein Y is alkyl, alkoxy, alkoxyalkyl, chloro, fluoro, bromo or carboxamidoalkyl and $R^1$ is hydrogen, alkyl, alkoxy, alkylthio, alkoxycarbonyl, chloro, fluoro or dialkylamino, m is 0-2, $R^2$ is branched alkyl and Het is an aromatic heterocycle. The acetylenes are useful in treating hypertension and/or angina.

20 Claims, No Drawings

HETEROAROMATIC ACETYLENES USEFUL AS ANTIHYPERTENSIVE AGENTS

The present invention comprises certain 1-phenoxy-2-propanols wherein the phenyl group is substituted at the 2-position with a heterocyclic acetylene group. Such compounds are useful in the treatment of hypertension.

At pages 182-188 of the Journal of Medicinal Chemistry, Vol. 21, No. 2 (1978), M. T. Cox et al., describes a class of linked aryl aryloxypropanols which do not show any significant $\beta$-blocking activity. Two of the listed compounds are linked via an acetylenic moiety. In addition, U.S. Pat. No. 4,010,158 discloses 1-(2'-ethynylphenoxy)-2-hydroxy-3-butylaminopropanes useful as $\beta$-adrenergic receptor blocking agents. A cursory listing of about 600 acetyleneic structures is made in U.S. Pat. No. 4,412,856 and several acetylenes are described in German Offenlegungsschrift No. 25 03 222. Certain olefins are shown in German Offenlegungsschrift No. DE 30 06 351.

SUMMARY OF THE INVENTION

Heteroaromatic acetylenes having the formula (I):

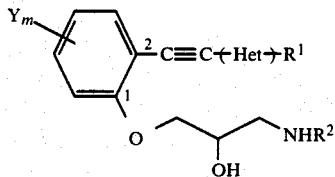

where Het is an aromatic heterocycle selected from pyridinyl, thienyl, furanyl, pyrrolyl, pyrazolyl, isoxazolyl, pyrazinyl, pyrimidinyl, indolyl, quinolyl or isoquinolyl, Y and $R^1$ are substituents, Y is 0-2 and $R^2$ is an alkyl group which is branched in at least the $\alpha$ position.

DETAILED DESCRIPTION OF THE INVENTION

Compounds of the invention are of the following formula (I):

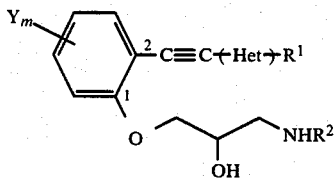

wherein
Y is alkyl, alkoxy, alkoxyalkyl, chloro, fluoro, bromo or carboxamidoalkyl;
m is 0, 1 or 2;
$R^1$ is hydrogen alkyl, alkoxy, alkylthio, alkoxycarbonyl, chloro, fluoro or dialkylamino;
$R^2$ is branched chain alkyl of about 3 to 7 carbons with the carbon alpha to the nitrogen atom being branched; and
Het is pyridinyl, thienyl, furanyl, pyrrolyl, pyrazolyl, isoxazolyl, pyrazinyl, pyrimidinyl, indolyl, quinolyl or isoquinolyl; and the pharmaceutically acceptable acid addition salts thereof.

In addition to the above, Y may be cycloalkyl, hydroxy, trifluoromethyl, alkylthio, alkenyl, alkynyl, alkenyloxy, alkynyloxy, alkylthioalkyl, alkanoyl, alkanoyloxy, alkanoylamino, alkanoylaminoalkyl, carboxamido, N-alkylcarboxamido, N,N-dialkylcarboxamido, phenyl or alkylsulfonylamino.

Y, in particular, is alkyl of about 1 to 6 carbons such as methyl, ethyl or iso-propyl; alkoxy of about 1 to 6 carbons such as methoxy, ethoxy or iso-propoxy; alkoxyalkyl of about 2 to 8 carbons such as ($C_{1-4}$ alkoxy) $C_{1-4}$ alkyl, e.g. methoxymethyl; chloro; fluoro; bromo; or carboxamidoalkyl of about 2 to 7 carbons of the formula $-(C_{1-6}$ Alkyl$)CONH_2$, e.g. $-CH_2CONH_2$.

m is 0, 1 or 2 and 0 or 1 in particular, e.g. m=0.

$R^1$, in particular, is hydrogen; alkyl of about 1 to 6 carbons such as methyl, ethyl or iso-propyl; alkoxy of about 1 to 6 carbons such as methoxy, ethoxy or iso-propoxy; alkylthio of about 1 to 6 carbons such as methylthio or ethylthio; alkoxycarbonyl of about 2 to 7 carbons such as methoxycarbonyl ($-COOCH_3$) or ethoxycarbonyl ($-COOCH_2CH_3$); chloro; fluoro; or dialkylamino of about 2 to 8 carbons, e.g. dimethylamino, N-methyl, N-ethylamino or N,N-di-tert-butylamino. $R^1$ may be attached at any open position on the heterocyclic ring, in particular, at a position other than the position of attachment of acetylene.

$R^2$, in particular, is iso-propyl, sec-butyl or tert-butyl. In any cse, the alpha ($\alpha$) carbon of $R^2$ which is next to the nitrogen, i.e., $-CH_2-NH-C_\alpha-C_\beta-$ etc., has at least 2 carbons attached to it, e.g. $-CH_2-NH-C_\alpha-(C_{\beta 1})-C_\beta$. Thus, there are 2 or 3 carbons attached to the carbon of $R^2$ next to the $-NH$ group.

Het is 2-, 3- or 4-pyridinyl; 2- or 3-thienyl; 2- or 3-furanyl; 2- or 3-pyrrolyl; 3-, 4- or 5-pyrazolyl; 3-, 4- or 5-isoxazolyl; 2-pyrazinyl; 2-, 4- or 5-pyrimidinyl; 1-, 2-, 3-, 4-, 5-, 6- or 7-indolyl, particularly 2-, 3- or 5-indolyl; 2-, 3-, 4-, 5-, 6-, 7- or 8-quinolyl; or 1-, 3-, 4-, 5-, 6-, 7- or 8-isoquinolyl. As used in this and the following paragraph, the number preceding the heterocyclic name refers to the position of attachment to the acetylene group.

In particular, Het is a pyridinyl; thienyl, e.g. 2-thienyl; furanyl, e.g. 2-furanyl; pyrimidinyl, e.g. 5-pyrimidinyl; or indolyl, e.g. 5-indolyl group, e.g. a 3- or 4-pyridinyl group. As used in this specification with respect to attachment of the heterocycle, the numbering system conforms to the generally accepted designations such as in "The Principles of Heterocyclic Chemistry" by A. R. Katritzky et al., Academic Press, New York (1968). When present in a particular molecule with substituents on the heterocycle, the number position of the attachment to the acetylene may vary, as determined by CAS nomenclature.

Compounds of formula (I) and other compounds of the invention may exist in various isomeric forms, e.g. in view of the presence of an asymmetric carbon, e.g. the carbon attached directly to the NH group. It is understood that the present invention includes all such individual enantiomeric and diasteriomeric isomers and their racemates. Also within the scope of the invention are compounds of the invention in the form of hydrates and other solvate forms. "Alkyl" as used herein is indicative of straight and branched chain alkyl.

Representative salts of compounds of formula (I) which may be used include those made with acids such as hydrochloric, hydrobromic, hydroiodic, perchloric sulfuric, nitric, a phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluenesulfonic, cyclohexanesulfamic, salicylic, p-aminosalicylic, 2-phenoxybenzoic, 2-acetoxybenzoic or a salt made with saccharin. The salts may be prepared by reacting the corresponding free base of formula (I) with the acid and then recovering the salt.

Particular compounds of the invention of formula (I) include the following, prepared as described hereinafter in the Examples, respectively:

1-[(1,1-dimethylethyl)amino]-3-[2-(4-pyridinylethynyl)-phenoxy]-2-propanol;

1-[(1,1-dimethylethyl)amino]-3-[b  2-(3-pyridinylethynyl)phenoxy]-2-propanol;

1-[(1,1-dimethylethyl)amino]-3-[2-(2-pyridinylethynyl)-phenoxy]-2-propanol;

1-[(1,1-dimethylethyl)amino]-3-[5-(2-pyrimidinylethynyl)phenoxy]-2-propanol;

1-[(1,1-dimethylethyl)amino]-3-[2-(2-thienylethynyl)-phenoxy]-2-propanol;

ethyl 5-[[2-[3-[(1,1-dimethylethyl)amino-2-hydroxyproxy]phenyl]ethynyl]-2-furancarboxylate;

1-[(1,1-dimethylethyl)amino]-3-[2-[[2-methyl-3-(methylthio)-1H-indol-5-yl]ethynyl]phenoxy]-2-propanol;

1-[(1,1-dimethylethyl)amino]-3-[2-(pyrazinylethynyl)-phenoxy]-2-propanol;

1-[(1-methylethyl)amino]-3-[2-(4-pyridinylethynyl)-phenoxy]-2-propanol; and

1-[(1,1-dimethylethyl)amino]-3-[2-(4-pyrazolylethynyl)-phenoxy-2-propanol.

In preparing a compound of formula (I) according to the following Reaction Scheme, a phenol (II) is halogenated (X=Br or I) in the ortho position to give an ortho halophenol (III) wherein X is Br or I. In order to induce the halogen to enter into the ortho position, the phenolate anion is the species which is halogenated, see Machacek, Sterba and Valter, Collection Czechslav. Chem. Commun., 37, 3073 (1972). The halogenation can be carried out by generating the phenolate anion, for instance with sodium hydride, an alkali metal alkoxide or an alkali metal hydroxide followed by adding a halogenating agent such as iodine or bromine. The halogenation is preferably carried out in an inert solvent such as toluene, benzene or a halocarbon. The halogenation may be performed over a temperature range of −40° to 50° C. When the position para to the phenol group is blocked by the presence of a Y substituent, the ortho halogenation may be carried out on then phenol itself by halogenating agents such as iodine monochloride, iodine-nitric acid, iodine-mercuric oxide, bromine, pyridinimum bromide perbromide or cupric bromide. The ortho halophenol (III) where X is Br or I is then alkylated with epichlorohydrin in the presence of base to give the epoxide (IV). The bases employed may be alkali metal hydride, alkali metal alkoxides or alkali metal carbonates. The reaction may be carried out at ambient to elevated temperatures for example from about 25° to about 125° C. A period of heating may be required to convert the intermediate chlorohydrin to epoxide (IV), following the disappearance of (III). The reaction may be performed in any solvent generally used for alkylation reactions, for example lower alkanols, aromatic solvents or ethers. Especially advantageous due to higher rates of reaction are the dipolar aprotic solvents such as DMF, DMSO, sulfolane and methyl ethyl ketone. The opening of the epoxide (IV) by amines $R^2$ $NH_2$ to give ortho halophenoxy propanolamines (V) is carried out by heating the reactants in a lower alkanol or a dipolar aprotic solvent, e.g. methanol, ethanol, DMF, DMSO or sulfolane at 35° to 150° C. The coupling of ortho halophenoxy propanolamines (V) with a heteroaromatic ethyne, $R^1HetC\equiv CH$, to give a product a formula (I) is carried out with catalysis by a compound of palladium, for instance, tetrakistriphenylphosphine palladium (O), as described by Sonogashira et al., see Tetrahedron Lett. 4467 (1975). Cuprous salts may be added as co-catalysts. Compounds of formula (VI) may be prepared by coupling of 2-methyl-3-butyn-2-ol to formula (V) with palladium catalysis, again, as described by Sonogashira et al. Cleavage of acetone from compounds of formula (VI) by the action of bases such as alkali metal hydroxide or alkoxides with or without the presence of phase transfer catalysts produces the simple ethynyl compounds (VII). Preparation of compounds of formula (VII) is also described in U.S. Pat. No. 4,010,158. Coupling of a heteroarylhalide, $R^1HetX$, with a compound of formula (VII) with palladium catalysis as described by Sonograshira et al. produces the compounds of formula (I).

For the preparation of compounds of formula (I) where Het-$R^1$ contains an acidic hydrogen such as 4-pyrazolyl, it is necessary to proceed from (VII) to (I) via intermediates (VIII) and (IX) where the hydroxy is successively protected by a group $R^3$ ($R^3$=lower acyl, e.g. alkanoyl of 2 to 6 carbons such as acetyl, propionyl, or butyryl or trialkylsilyl, etc.), coupled with a heteroarylethyne and finally deprotected. The acyl protecting group for $R^3$ may be removed by mild alkaline hydrolysis and the trialkylsilyl group by mild acid hydrolysis or treatment by fluoride.

Reaction Scheme:

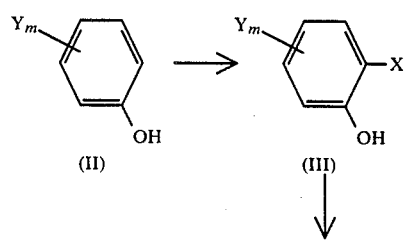

Reaction Scheme:

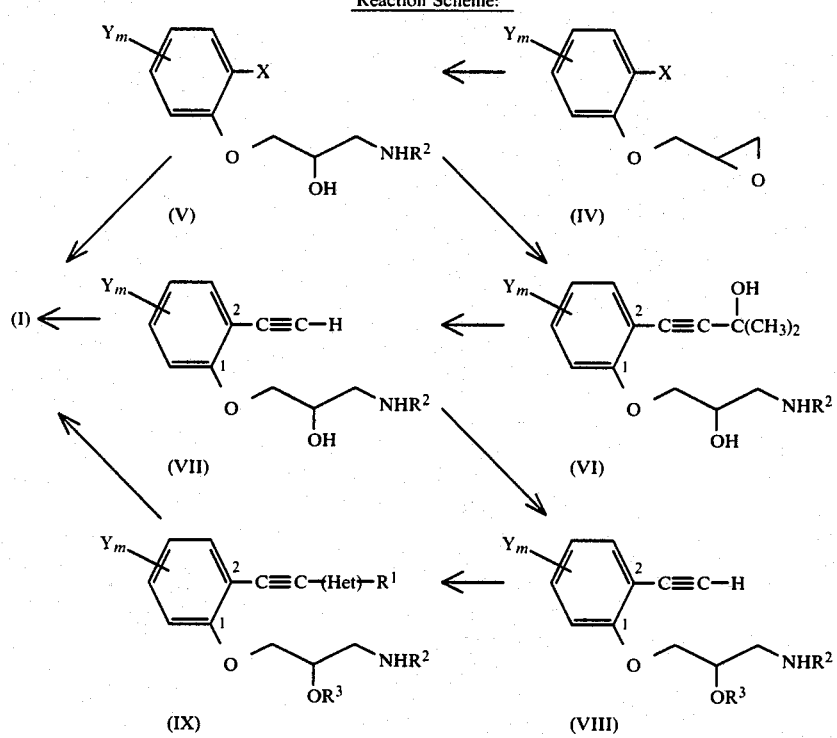

-continued

The activity of compounds of formula (I) for the treatment of hypertension may be determined using the Spontaneously Hypertensive Rat (SHR) test as described below.

In this test, the arterial pressure of adult spontaneously hypertensive rats (Charles River) is monitored directly via an aortic cannula. The SH rats are anesthetized with an inhalation anesthetic (ether). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. The test compounds are administered to at least 3 rats at doses selected in the range of 0.1 to 100 mg/kg of body weight by intraperitoneal (i.p.) or oral (p.o.) routes of administration. The arterial pressure and heart rate are monitored for a minimum of 24 hours. A test compound is considered to be active as an antihypertensive agent if the mean arterial pressure (MAP) indicates a fall of >15 mm of Hg. Each animal serves as its own control.

In addition to their utility in the treatment of hypertension, the compounds of formula (I) are useful in the treatment of the symptoms of angina pectoris by virtue of their ability to dilate coronary arteries. Often, peripheral arteries are also dilated by compounds which dilate coronary arteries and thus, this test is also useful for predicting activity as an antihypertensive. Compounds of the invention were tested in this regard in the "Langendorff's Isolated Heart" model as generally described in "Pharmacological Experiments on Isolated Preparations", Staff of the Department of Pharmacology, University of Edinbourgh, 2nd Ed., Churchill, Livingston, N.Y. (1970) pages 112–119.

A third system for determining the ability of compounds of the invention to act as anti-hypertensives is the Evaluation of Potential Beta Adrenergic Blocking Activity. Potential beta blocking activity was evaluated in two in vitro tests. The potential Beta-1 antagonistic activity was evaluated using isoproterenol induced tachycardia in guinea pig atrial pairs (a.). Beta-2 activity was evaluated using blockade of isoproterenol-induced relaxation of acetylcholine contracted tracheal rings (b.).

a. In vitro guinea pig atrial pairs: Female guinea pigs weighing 250–500 g were anesthetized in a carbon dioxide chamber, the chest was opened and the heart was carefully removed. The heart was then placed in cold Krebs-bicarbonate buffer in a Petri dish and the atria were carefully dissected. The atria were mounted in 50 ml baths in Krebs-bicarbonate buffer at 35° C., and airated with 95% $O_2$/5% $CO_2$. Contractions were monitored using a Narco isometric force transducer under 1.0 g tension. Rate was monitored using the output from the force transducer using a Narco Biotach. Recordings were made using a Narco Physiograph. Studies were done by doing multiple concentration response curves to isoproterenol using at least three concentrations of tests compounds. $ED_{50}$'s for isoproterenol tachycardia were constructed for the means of at least three experiments. $ED_{50}$'s were calculated using a relative potency program in the DEC 1099 (RELPOT) along with relative potencies.

The competitiveness of the antagonism, if any was determined by Schild plots using the Log (dose ratio-1) vs. -Log (concentration of antagonist). Propranolol was used as a positive control and potencies of test compounds were compared to it.

b. In vitro guinea pig tracheal rings: Guinea pigs were sacrificed in a carbon dioxide chamber and the trachea removed carefully. The trachea was cleaned and placed in a Petri dish with Kreb's Bicarbonate buffer. Rings of cartilage with attached smooth muscle were cut and chains of two or three rings were made by tying the rings together using silk thread. The chain was mounted in a 10 ml organ bath immersed in a water bath kept at 35° C. The chain was attached in a narco isometric force transducer and kept under 1 g tension. In order to evaluate the effects of the experimental compounds as Beta-2 antagonists the trachea were contracted with 1 μg/ml acetylcholine and increasing concentrations of isoproterenol were added at 5 minute intervals until the trachea was completely relaxed. Increasing doses of the test compound were given 5 minutes after acetylcholine and 5 minutes prior to the addition of cumulative doses of isoproterenol. Means and standard error from at least 3 experiments were calculated and $ED_{50}$'s for isoproterenol were determined using a relative potency program (RELPOT) on the DEC 1099. Competitiveness was determined as with the guinea pig atria pair study. Propranolol was used as a positive control and as the standard of reference for all active test compounds.

In view of testing carried out as described above on compounds of the invention, two of the best compounds of the invention are believed to be the compounds produced in Examples 1 and 2, i.e., of the formula (I) wherein m=0, $R^1$=H, $R^2$=tert-butyl, and Het is 4- or 3-pyridinyl. In the SHR test, these compounds were found to cause a marked and sustained reduction of hypertensive blood pressure (−46 and −54 mm Hg; duration 7.5 and 10.5 hours, respectively) when compared at the same oral dose (30 mg/kg). Heart rate was reduced (−87 and −41 beats/min, respectively), indicating lack of reflex tachycardia.

For the treatment of hypertension or angina, compounds of the present invention of the formula (I) may be administered orally or parenterally, preferably internally, in a pharmaceutical composition comprising about 1 to 2,000 mg, preferably about 30 to 400 mg of one or more of the acetylene compounds per day for an average adult human depending on the activity of the particular compound chosen. The dosage may be divided into 1 to 4 unit dosage forms per day. While the therapeutic methods of the invention are most useful for human subjects in need of alleviation of hypertension or angina, the compounds may be administered to other mammals at comparable dosages per weight of the subject.

Pharmaceutical compositions containing the acetylene compounds of the present invention of formula (I) or an acid addition salt thereof as the active ingredient may be prepared by intimately mixing the acetylene compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonful, tablespoonful and the like, and segregated multiples thereof.

In addition to pharmaceutical compositions and method for the treatment of hypertension, also part of the present invention are the novel intermediates described herein, e.g. of formula (IX).

In the following Examples and throughout the specification, the following abbreviations may be used: E (trans); Z (cis); bp (boiling point); mp (melting point); g (grams); mL (milliliters); μ(microliters); hplc (high pressure liquid chromatography); glc (gas liquid chromatography); N (normal); M (molar); μM (micromolar); mM (millimolar); mmole (millimoles); hr (hours); min (minutes); d (decomposed); THF (tetrahydrofuran); MeOH (methanol); DMF (dimethylformamide); Ph (phenyl); mg (milligrams); mm (millimeters); p.o. (per os); and C, H, N. etc. (the chemical symbols for the elements). Unless otherwie indicated, all temperatures are reported in degrees centrigrade (°C.) and all pressures in mm of mercury.

EXAMPLE 1

1-[(1,1-Dimethylethyl)amino]-3-[2-(4-pyridinylethynyl)phenoxy]-2-propanol (E)-2-Butenedioate A 6.1 g sample of 1-[(1,1-dimethylethyl)amino]-3-(2-ethynylphenoxy)-2-propanol (24.7 mmole) and a 5.8 g (37 mmole) sample of 4-bromopyridine were dissolved in 24 mL of triethylamine and 24 mL of THF. The solution was degassed by passage of nitrogen gas. A 0.14 g sample (0.11 mmole) of tetrakis(triphenylphosphine)palladium(O) and a 0.05 g sample (0.26 mmole) of copper (I) iodide were added. The mixture was allowed to stir for 18 hr under $N_2$. The solvent was evaporated in vacuo at 25°. The residue was partitioned between ether and dilute NaOH solution. The organic layer was separate, washed with water and brine, dried ($K_2CO_3$) and the solvent evaporated in vacuo to give a semisolid. This residue was chromatographed on a Waters "Prep 500" preparative hplc. The column was eluted with $CH_2Cl_2$/MeOH/$NH_4OH$ in a ratio of 90/9/1. The product bearing fractions were pooled. The solvent was evaporated in vacuo at 25° C. A fumarate salt was prepared in MeOH. The MeOH was evaporated in vacuo and the residue crystallized from 2-propanol. There was obtained a 37% yield of the title compound as a white crystalline solid, mp 179°–180° (d).

EXAMPLE 2

1-[(1,1-Dimethylethyl)amino]-3-[2-(3-pyridinylethynyl)phenoxy]-2-propanol Hydrochloride Hydrate (4:4:1)

Using the procedures of Example 1 and employing an equivalent quantity of 3-bromopyridine in place of 4-bromopyridine, there was obtained a 25% yield of the title compound as a white crystalline solid, mp 145°–7° C.

EXAMPLE 3

1-[(1,1-Dimethylethyl)amino]-3-[2-(2-pyridinylethynyl)phenoxy]-2-propanol Hydrochloride Using the procedure of Example 1 and employing an equivalent quantity of 2-bromopyridine in place of 4-bromopyridine, there was obtained a 52% yield of the title compound as a white crystalline solid, mp 198°–200° C.

EXAMPLE 4

1-[(1,1-Dimethylethyl)amino]-3-[5-(2-pyrimidinylethynyl)phenoxy]-2-propanol Hydrochloride Using the procedure of Example 1 and employing an equivalent quantity of 5-bromopyrimidine in place of 4-bromopyridine, there was obtained a 37% yield of the title compound as an off white solid, mp 191°–193° C.

EXAMPLE 5

1-[(1,1-Dimethylethyl)amino]-3-[2-(2-thienylethynyl)phenoxy]-2-propanol Hydrochloride Using the procedure of Example 1 and employing an equivalent quantity of 2-iodothiophene in place of 4-bromopyridine, there was obtained a 45% yield of the title compound as a white crystalline solid, mp 168°–171° C.

EXAMPLE 6

Ethyl 5-[[2-[3-[(1,1-Dimethylethyl)amino]-2-hydroxyproxy]phenyl]ethynyl]-2-furancarboxylate (E)-2-Butenedioate (5:3)

Using the procedure of Example 1 and employing an equivalent quantity of ethyl 5-bromofuran-2-carboxylate in place of 4-bromopyridine, there was obtained at 29% yield of the title compound as a white crystalline solid, mp 183.5°–185.5° C.

EXAMPLE 7 a.

5-Iodo-2-methyl-3-methylthio-1H-indole

A solution of 10.9 g (91 mmole) of 5-butylhypochlorite in 40 mL of CH$_2$Cl$_2$ was added dropwise to a solution of 20.0 g (91 mmole) of 4-iodoaniline in 300 mL of CH$_2$Cl$_2$ at −70° C. After 10 min, a solution of 7.43 mL (91 mmole) of methylthioacetone in 40 mL of CH$_2$Cl$_2$ was added dropwise. After stirring for 90 min, 12.7 mL of triethylamine was added. The reaction was allowed to warm to room temperature. The mixture was washed with water, dried (K$_2$CO$_3$) and the solvent evaporated in vacuo. The residue was extracted with hot hexane. The precipitated crystals were collected to give 2.95 g (11% yield) of the title compound. The mp after recrystallization from CH$_2$Cl$_2$-hexane was 95°–97° C.

b.

1-[(1,1-Dimethylethyl)amino]-3-[2-[[2-methyl-3-(methylthio)-H-indol-5-yl]ethynyl]phenoxy]-2-propanol Using the procedure of Example 1 and employing an equivalent quantity of 5-iodo-2-methyl-3-methylthio-1H-indole in place of 4-bromopyridine there was obtained a 30% yield of the title compound as off white crystals, mp 155°–157° C.

EXAMPLE 8

1-[(1,1-Dimethylethyl)amino]-3-[2-(2-pyrazinylethynyl)phenoxy]-2 propanol Hydrochloride Using the process of Example 1 and employing an equivalent of 2-chloropyrazine in place of 4-bromopyridine there was obtained a 40% yield of the title compound as a white crystalline solid, m.p. 219°–221° C.

EXAMPLE 9 a.

[(2-iodophenoxy)methyl]oxirane

To a round bottom flask under N$_2$ was added 4.56 g (0.095 mole) of 50% NaH in oil. The NaH was washed twice with hexane, then 220 ml of DMF was added. Aliquots of 20.0 g (0.091 mole) of o-iodophenol were added over 15 minutes then 30.0 ml (0.450 mole) of epichlorohydrin was added and the solution heated to 70° C. After two hours the reaction was evaporated in vacuo, taken into CHCl$_3$, washed with 10% NaOH, water, and brine and dried with MgSO$_4$. The solvent was evaporated in vacuo to give 24.93 g of crude product. Distillation at 110°–114° C., 0.05 mm Hg gave 20.0 g (80.0%) of [(2-iodophenoxy)methyl]-oxirane.

b.

1-[(1-Methylethyl)amino]-3-(2-iodophenoxy)-2-propanol Hydrochloride

A 7.91 g (93 mmole) sample of 2-propylamine was added to a solution of 15.5 g (58 mmole) of [(2-iodophenoxy)methyl]oxirane in 120 mL of absolute ethanol. The mixture was heated under reflux for 18 hr. The solvent was evaporated and the residue recrystallized twice from methylcyclohexane. The crystalline base was converted to the hydrochloride salt by treatment with ethereal hydrogen chloride. There was obtained the title compound as a white crystalline solid, m.p. 153°–155° C.

c.

1-[(1-Methylethyl)amino]-3-[2-(4-pyridinylethynyl)phenoxy]-2-propanol-(E)-2-Butenedioate A solution of 8.38 g (25 mmole) 1-[(1-methylethyl)amino]-3-(2-iodophenoxy)-2-propanol in 25 mL of triethylamine and 47 mL of THF was degassed by admission of N$_2$. To the solution was added 3.17 g (27.5 mmole) of 4-ethynylpyridine, 0.14 g (0.125 mmole) (Ph$_3$P)$_4$Pd and 0.05 g (0.25 mmole) CuI. The reaction was stirred for 20 hr. The mixture was partitioned between CH$_2$Cl$_2$ and water and the CH$_2$Cl$_2$ layer concentrated to dryness. The residue water dissolved in ether, washed with dilute NaOH solution then dilute HCl. The HCl extract was made basic with NaOH solution. The mixture was extracted with ether. The ether layer was washed with brine, dried (K$_2$CO$_3$) and evaporated in vacuo to an oil. The oil water chromatographed on a "Waters 500 Prep" preparative hplc using CH$_2$Cl$_2$:CH$_3$OH:NH$_4$OH, 93:6:1 as eluant. The product bearing fractions were pooled and the solvent evaporated in vacuo. A fumarate salt was prepared from 2-propanol. It was recrystallized to give 4.0 g (38% yield of the title compound as a white crystalline solid, m.p. 186°–187° C.

EXAMPLE 10 a.

1-[(1,1-Dimethylethyl)amino]-3-(2-ethynylphenoxy)-2-propanol Acetate

A 4.8 g (42.8 mmole) sample of 1-acetylimidazole was added to a solution of 5.14 g (20.8 mmole) of 1-[(1,1-dimethylethyl)amino]-3-(2-ethynylphenoxy)-2-propanol in 28 ml THF. The mixture was stirred under $N_2$ for one hour. The mixture was partitioned between water and ether. The ether layer was washed with brine, dried ($K_2CO_3$) and the solvent evaporated in vacuo to give the title compound as an oil, 6.14 g.

b.

1-Acetyl-4-[[2-[2-(acetyloxy)-3-[(1,1-dimethylethylamino]propoxy]phenyl]ethynyl]-1H pyrazole A solution of 6.14 g (20.8 mmole) of the freshly prepared crude product from example 10a, 5.40 g (22.9 mmole) of 4-iodo-1-acetylpyrazole in 20 ml THF, 20 ml triethylamine was degassed by admission of $N_2$. A 0.12 g (0.1 mmole) sample of $(Ph_3P)_4Pd$ and a 0.04 g (0.2 mmole) sample of CuI were added. An exotherm occurred. The mixture was stirred without external heating for one hour. The mixture was partitioned between water and $CH_2Cl_2$. The $CH_2Cl_2$ layer was evaporated in vacuo. The residue was partitioned between ether and dilute sodium hydroxide. The ether layer was extracted with dilute HCl. The aqueous layer was made basic with dilute NaOH. The mixture was extracted with ether. The ether layer was washed with brine, dried ($K_2CO_3$) and evaporated to give 7.7 g (94% yield) of the title compound as an oil.

c.

1-[(1,1-Dimethylethyl)amino]-3-[2-(4-pyrazolylethynyl)phenoxy-2-propanol (E)Butenedioate [1:1]

A solution 7.49 g (18.9 mmole) of the product of Example 10b and 1.58 g (23.9 mmole) of KOH in 25 ml of MeOH was stirred for 30 min. The solvent was partially evaporated in vacuo. The mixture was partitioned between water and ether. The ether layer was washed with brine, dried ($K_2CO_3$) and concentrated to dryness. A fumarate salt was prepared out of methanol and the solid recrystallized from MeOH/2-PrOH to give 3.34 g (42% yield of the title compound as a white solid, m.p. 208°–210° C.

What is claimed is:

1. A heteraromatic acetylene of the following formula (I):

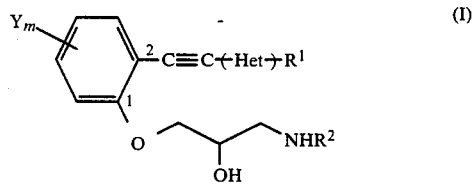

wherein

Y is alkyl of about 1 to 6 carbons, alkoxy of about 1 to 6 carbons, alkoxyalkyl of about 2 to 8 carbons, chloro, fluoro, bromo or carboxamidoalkyl of about 2 to 7 carbons;

m is 0, 1 or 2;

$R^1$ is hydrogen, alkyl of about 1 to 6 carbons, alkoxy of about 1 to 6 carbons, alkylthio of about 1 to 6 carbons, alkoxycarbonyl of about 2 to 7 carbons, chloro, fluoro or dialkylamino of about 2 to 8 carbons;

$R^2$ is branched chain alkyl of about 3 to 7 carbons with the carbon alpha to the nitrogen atom being branched; and Het is pyridinyl, pyrrolyl or pyrazolyl; and the pharmaceutically acceptable acid addition salts thereof.

2. The acetylene of claim 1, wherein Het is 2-pyridinyl.

3. The acetylene of claim 2, wherein Het is pyrrolyl.

4. The acetylene of claim 1, wherein Het is 3- or 4-pyridinyl.

5. The acetylene of claim 1, wherein Het is 3-pyridinyl.

6. The acetylene of claim 1, wherein Het is 4-pyridinyl.

7. The acetylene of claim 1, wherein Het is pyrazolyl.

8. The acetylene of claim 1, wherein $R^2$ is iso-propyl, sec-butyl or tert-butyl.

9. The acetylene of claim 1, wherein $R^1$ is hydrogen.

10. The acetylene of claim 1, wherein m is 0.

11. The acetylene of claim 1, wherein m is 0; and $R^1$ is hydrogen.

12. The acetylene of claim 1, wherein said acetylene is selected from the group consisting of:
1-[(1,1-dimethylethyl)amino]-3-[2-(4-pyridinylethynyl)-phenoxy]-2-propanol;
1-[(1,1-dimethylethyl)amino]-3-[2-(3-pyridinylethynyl)-phenoxy]-2-propanol;
1-[(1,1-dimethylethyl)amino]-3-[2-(2-pyridinylethynyl)-phenoxy]-2-propanol;
1-[(1-methylethyl)amino]-3-[2-(4-pyridinylethynyl)-phenoxy]-2-propanol; and
1-[(1,1-dimethylethyl)amino]-3-[2-(4-pyrazolylethynyl)-phenoxy-2-propanol, and
their pharmaceutically acceptable acid addition salts.

13. The acetylene of claim 1, wherein said acetylene is 1-[(1,1-dimethylethyl)amino]-3-[2-(4-pyridinylethynyl)phenoxy]-2-propanol or a pharmaceutically acceptable acid addition salt thereof.

14. The acetylene of claim 1, wherein said acetylene is 1-[(1,1-dimethylethyl)amino]-3-[2-(3-pyridinylethynyl)phenoxy]-2-propanol or a pharmaceutically acceptable acid addition salt thereof.

15. The acetylene of claim 1, wherein said acid-addition salt is a salt with an acid selected from the group consisting of hydrochloric, hydrobromic, hydroiodic, perchloric, sulfuric, nitric, a phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluene sulfonic, cyclohexanesulfamic, salicylic, p-aminosalicylic, 2-phenoxybenzoic, 2-acetoxybenzoic or a salt made with saccharin.

16. An antihypertensive pharmaceutical composition comprising an antihypertensive amount of an acetylene of claim 1 and a pharmaceutically acceptable diluent or carrier.

17. A method of treating hypertension in a mammal which comprises administering to the mammal, the pharmaceutical composition of claim 16.

18. The method of claim 17, wherein said mammal is a human.

19. An acetylene of the following formula (IX):

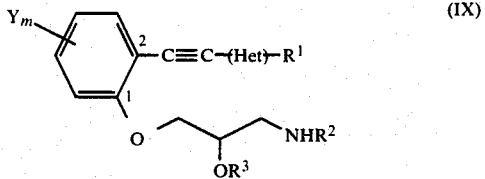

wherein

Y is alkyl of about 1 to 6 carbons, alkoxy of about 1 to 6 carbons, alkoxyalkyl of about 2 to 8 carbons, chloro, fluoro, bromo or carboxamidoalkyl of about 2 to 7 carbons;

m is 0, 1 or 2;

$R^1$ is hydrogen, alkyl of about 1 to 6 carbons, alkoxy of about 1 to 6 carbons, alkylthio of about 1 to 6 carbons, alkoxycarbonyl of about 2 to 7 carbons, chloro, fluoro or dialkylamino of about 2 to 8 carbons;

$R^2$ is branched chain alkyl of about 3 to 7 carbons with the carbon alpha to the nitrogen atom being branched; and Het is pyridinyl pyrrolyl or pyrazolyl; and $R^3$ is a alkanoyl of 2-6 carbon atoms or trialkylsilyl protecting group, and the acid addition salts thereof.

20. The acetylene of claim 19, wherein $R^3$ is acetyl, propionyl or butyryl.

* * * * *